(12) United States Patent
Hung

(10) Patent No.: US 6,642,009 B2
(45) Date of Patent: *Nov. 4, 2003

(54) ISOLATED DUCTAL FLUID SAMPLE

(75) Inventor: David Hung, Belmont, CA (US)

(73) Assignee: Cytyc Health Corporation, Boxborough, MA (US)

( * ) Notice: Subject to any disclaimer, the term of this patent is extended or adjusted under 35 U.S.C. 154(b) by 29 days.

This patent is subject to a terminal disclaimer.

(21) Appl. No.: 09/800,970

(22) Filed: Mar. 8, 2001

(65) Prior Publication Data

US 2001/0034038 A1 Oct. 25, 2001

Related U.S. Application Data

(63) Continuation-in-part of application No. 09/625,399, filed on Jul. 26, 2000, which is a continuation-in-part of application No. 09/502,404, filed on Feb. 10, 2000, which is a continuation-in-part of application No. 09/313,463, filed on May 17, 1999, now abandoned, application No. 09/800,970, which is a continuation-in-part of application No. 09/473,510, filed on Dec. 28, 1999, now Pat. No. 6,413,228.

(60) Provisional application No. 60/166,100, filed on Nov. 17, 1999.

(51) Int. Cl.$^7$ .............................................. G01N 33/53

(52) U.S. Cl. .......................... 435/7.21; 435/6; 435/7.1; 435/7.2; 435/7.9; 436/63

(58) Field of Search ............................. 435/6, 7.1, 7.2, 435/7.21, 7.5, 7.8, 7.9–7.95, 960; 436/63, 64

(56) References Cited

U.S. PATENT DOCUMENTS

| | | |
|---|---|---|
| 6,221,622 B1 | 4/2001 | Love |
| 6,413,228 B1 | 7/2002 | Hung et al. |

FOREIGN PATENT DOCUMENTS

| | | |
|---|---|---|
| EP | 0 502 485 B1 | 10/1996 |
| EP | 1 182 459 | 2/2002 |
| WO | WO 97/48805 | 12/1997 |
| WO | WO 98/07857 | 2/1998 |
| WO | WO 98/08976 | 3/1998 |
| WO | WO 99/55384 | 11/1999 |
| WO | WO 00/42841 | 7/2000 |
| WO | WO 00/70349 | 11/2000 |

OTHER PUBLICATIONS

JAMA vol. 224 p. 823 (1973).*
Jin et al Chinese Tumor Clinical Medicine vol. 23 p. 381 (1996).*
Rao et al CAncer, Epidemiology and Prevention vol. 7 p. 1027 (1998).*
Hou et al, Radiology vol. 195 p. 568 (1995).*
Leborgne, Intraductal Biopsy of Certain Pathologic Processes of the Breast, Surgery 19:47–54 (1946).

Papanicolaou et al., Exfoliative Cytology of the Human Mammary Gland and Its Value in the Diagnosis of Cancer and Other Diseases of the Breast, Cancer 11:377–409 (1958).
Buehring, Screening for Breast Atypias Using Exfoliative Cytology, Cancer 43(5):1788–1799 (1979).
Makita et al., Duct Endoscopy and Endoscopic Biopsy in the Evaluation of Nipple Discharge, Breast Cancer Research and Treatment 18:179–188 (1991).
Jin et al., Study of Tumor Markers in Mammary Ductal Lavage for Early Detection of Breast Carcinoma, Zhongguo Zhong Liu Lin Chuang 23(6):381–385 (1996), with English translation.
Love et al., Breast–Duct Endoscopy to Study Stages of Cancerous Breast Disease, Lancet 348:997–999 (1996).
Sauter et al., Nipple Aspirate Fluid: A Promising Non–Invasive Method to Identify Cellular Markers of Breast Cancer Risk, British J. Cancer 76(4):494–501 (1997).
Papanicolaou et al, "Exfoliative Cytology of the Human Mammary Gland and Its Value in the Diagnosis of Cancer and Other Diseases of the Breast", pp 377–409, Mar./Apr. 1958.
Petrakis, "Physiological, biochemical, and cytological aspects of nipple aspirate fluid", Breast Cancer Research and Treatment, vol. 8, pp 7–19, 1886.
Petrakis, "Studies on the epidemiology and natural history of benign breast disease and breast cancer using nipple aspirate fluid", Cancer Epidemiology, Biomarkers and Prevention, vol. 2, pp 3–10, Jan/Feb 1993.
Petrakis, "Nipple Aspirate Fluid in Epidemiological Studies of Breast Disease", Epidemiologic Reviews, vol. 15, pp 188–195, 1993.
Sauter et al, "Nipple aspirate fluid: a promising non–invasive method to identify cellular markers of breast cancer risk", British Journal of Cancer, vol. 76(4), pp 494–501, 1997.
Imayama et al, Presence of Elevated Carcinoembryonic Antigen on Absorbent Disks Applied to Nipple Area of Breast Carcinoma Patients, Cancer, vol. 78, pp 1229–1234, 1996.
Cassels, D., "New tests may speed breast cancer detection", The Medical Post, Mar. 1973.
Love and Barsky, "Breast–duct endoscopy to study stages of cancerous breast disease", Lancet, vol. 348(9033), pp 997–999, 1996.

(List continued on next page.)

*Primary Examiner*—Sheela Huff
(74) *Attorney, Agent, or Firm*—Banner & Witcoff, Ltd.

(57) ABSTRACT

A sample for diagnosis of breast cancer can be prepared by isolating a ductal fluid sample from one duct of a breast of a patient. The isolated ductal fluid is not mixed with ductal fluid from any other duct of the breast. Generally the target duct is not spontaneously discharging. The isolated ductal fluid sample can be examined to determine the presence or absence of a marker associated with cancer or pre-cancer. An isolated ductal fluid sample not mixed with ductal fluid from any other duct of the breast permits identification of the duct which is diseased and provides increased sensitivity for existing diagnostic and analytic techniques.

23 Claims, No Drawings

OTHER PUBLICATIONS

Makita et al, Breast Cancer Res Treat, vol. 18, pp 179–188, 1991.

Fabian et al, Biomarker and Cytologic Abnormalities in Women at High and Low Risk for Breast Cancer, J. Cellular Biochemistry, vol. 17G, pp 153–16, 1993.

Wrensch et al, Breast Cancer Incidence in Women with Abnormal Cytology in Nipple Aspirates of Breast Fluid, Am J. Epidem, vol. 135, pp 130–141, 1992.

Goodson WH & King EB, Chapter 4: Discharges and Secretions of the Nipple, The Breast: Comprehensive Management of Benign and Malignant Diseases, $2^{nd}$ Ed. Vol. 2, Bland & Kirby eds.W. B. Saunders Col, Philadelphia, PA, pp 51–74, 1998.

Sartorius et al, Cytologic Evaluation of Breast Fluid in the Detection of Breast Disease, J. Natl Cancer Inst, vol. 59, pp 1073–1080, 1977.

King et al, Nipple Aspirate Cytology for the Study of Breast Cancer Precursors, JNCL, vol. 71(6), pp 1115–1121, 1983.

Frykberg and Masood, Copeland EM 3d. Bland Kl., (Ductal carcinoma in situ of the breast) Surgery, Gynecology & Obstetrics, vol. 177(4), pp 425–440, 1993.

\* cited by examiner

ISOLATED DUCTAL FLUID SAMPLE

CROSS-REFERENCES TO RELATED APPLICATIONS

This application is a continuation-in-part of application Ser. No. 09/625,399 filed Jul. 26, 2000, which is a continuation-in-part of application Ser. No. 09/502,404, filed on Feb. 10, 2000, which was a continuation-in-part of application Ser. No. 09/313,463, filed on May 17, 1999, now abandoned. This application is also a continuation-in-part of application Ser. No. 09/473,510, filed on Dec. 28, 1999, now U.S. Pat. No. 6,413,228 issued Jul. 2, 2002. This application also claims the benefit under 37 CFR 1.78 of provisional application 60/166,100 filed on Nov. 17, 1999. The full disclosures of each of the prior applications are incorporated herein by reference.

BACKGROUND OF THE INVENTION

For several decades significant members of the medical community dedicated to studying breast cancer have believed and shown that the cytological analysis of cells retrieved from nipple discharge from the breast milk ducts can provide valuable information for identifying patients at risk for breast cancer. Papanicolaou himself contributed to the genesis of such a possibility of a "Pap" smear for breast cancer by analyzing the cells contained in nipple discharge. See Papanicolaou et al, "Exfoliative Cytology of the Human Mammary Gland and Its Value in the Diagnosis of Cancer and Other Diseases of the Breast" Cancer (1958) March/April 377–409. See also Petrakis, "Physiological, biochemical, and cytological aspects of nipple aspirate fluid", *Breast Cancer Research and Treatment* 1986; 8:7–19; Petrakis, "Studies on the epidemiology and natural history of benign breast disease and breast cancer using nipple aspirate fluid" *Cancer Epidemiology, Biomarkers and Prevention* (Jan/Feb 1993) 2:3–10; Petrakis, "Nipple Aspirate Fluid in epidemiological studies of breast disease", *Epidemiologic Reviews* (1993) 15:188–195. More recently, markers have also been detected in nipple fluid. See Sauter et al, "Nipple aspirate fluid: a promising non-invasive method to identify cellular markers of breast cancer risk", *British Journal of Cancer* 76(4): 494–501 (1997). The detection of CEA in fluids obtained by a nipple blot is described in Imayama et al. (1996) *Cancer* 78: 1229–1234. Further, an intraductal aspiration method for cytodiagnosis in situations of spontaneous nipple discharge (Hou et al, Acta Cytologica 2000 v. 44:1029–1034) describes use of intraductal aspiration to collect specimens from spontaneously discharging ducts in order to make a cytodiagnosis.

Breast cancer is believed to originate in the lining of a single breast milk duct; and additionally the human breast is believed to contain from 6 to 9 of these ducts. See Sartorius, *JAMA* 224 (6): 823–827 (1973). Sartorius describes use of hair-like single lumen catheters that are inserted into breast ducts using an operating microscope and the ducts were flushed with saline solution as described in Cassels, D Mar. 20, 1973, The Medical Post, article entitled "New tests may speed breast cancer detection". After the fluid was infused, the catheter was removed because it was too small to collect the fluid, the breast was squeezed and fluid that oozed onto the nipple surface was removed from the surface by a capillary tube. Similarly, Love and Barsky, "Breast-duct endoscopy to study stages of cancerous breast disease", *Lancet* 348(9033): 997–999, 1996 describes cannulating breast ducts with a single lumen catheter and infusing a small amount of saline, removing the catheter and squeezing to collect the fluid that returns on the nipple surface. The use of a rigid 1.2 mm ductoscope to identify intraductal papillomas in women with nipple discharge is described in Makita et al (1991) *Breast Cancer Res Treat* 18: 179–188. It would be advantageous to collect the ductal fluid from within the duct and so facilitate duct-specific analysis.

SUMMARY OF THE INVENTION

It is an object of the invention to provide a method for preparing a sample for use in diagnosis of breast cancer or pre-cancer.

It is another object of the invention to provide an isolated ductal fluid sample suitable for analyzing breast cancer and pre-cancer.

It is yet another object of the invention to provide a method for analyzing breast markers or epithelial cells.

These and other objects of the invention are provided by one or more of the embodiments described below. In one embodiment a method is provided for preparing a sample for use in the diagnosis of breast cancer or pre-cancer. A ductal fluid sample is isolated from one duct of a breast of a patient. The isolated ductal fluid is not mixed with ductal fluid from any other duct of the breast.

According to another embodiment of the invention an isolated ductal fluid sample is provided. The sample is collected from a breast duct in a breast. The isolated ductal fluid is not mixed with ductal fluid from any other breast duct.

According to still another embodiment of the invention a method is provided for analyzing breast markers or epithelial cells. The presence or absence of a marker in an isolated ductal fluid sample is determined. The sample is collected from a breast duct in a breast. The isolated ductal fluid not mixed with ductal fluid from any other breast duct.

The present invention thus provides the art with improved samples and sampling techniques for diagnosing and prognosing breast cancer and pre-cancer.

DETAILED DESCRIPTION OF PREFERRED EMBODIMENTS OF THE INVENTION

The following preferred embodiments and examples are offered by way of illustration and not by way of limitation.

The invention comprises an isolated ductal fluid sample collected from a breast duct in a breast, the fluid not mixed with ductal fluid from any other breast duct. The isolated ductal fluid sample can be a sample from a non-discharging breast duct. A non-discharging duct is a breast duct that is not spontaneously discharging fluid or material, i.e., a duct which is not leaking fluid to the nipple surface. Spontaneously discharging ducts discharge fluid of various coloration. The spontaneous discharge itself is a warning sign usually requiring further investigation, such as, mammography, ductoscopy, and/or galactography. The present invention provides an isolated ductal fluid sample from a non-discharging duct, i.e., a ductal fluid and/or material sample, a portion of which would not otherwise have contacted the nipple surface. However, the isolated ductal fluid sample may also be from a discharging duct, provided the sample collected is not mixed with ductal fluid from any other duct.

The isolated ductal fluid sample can be examined for the presence of a marker, the absence of a marker, or the state or quality of a particular marker. The markers can comprise those detailed herein and related markers that indicate the status or condition of the breast. The marker status can be used to identify pre-cancer or cancer of the breast. The ductal fluid sample is collected from one duct of a breast of a patient. Ductal fluids may be collected from multiple ducts of a breast or from ducts in both breasts of a patient, e.g., in sequence, provided the fluid and material from each duct is kept separate for analysis from the other ducts. The ducts are also marked or otherwise identified so that follow-up and/or treatment of a duct that indicates the need for treatment can be conducted. The ductal fluid sample when collected or provided is not mixed with ductal fluid from any other duct of the breast.

The number of epithelial cells in a ductal fluid sample may range, for example, from a few to a hundred, to several hundred, to several thousand, and up to tens of thousands, e.g., 20,000 to 100,000 or more cells. At least ten epithelial cells are required to designate an isolated sample as adequate for analysis of the cells. An isolated ductal fluid sample can have 10 or more cells for analysis, and possibly a single clump of cells or more than one clump. A clump comprises a plurality of cells, generally at least about 4 to about 6 cells are in a clump, and the clump can comprise more cells than 6. Samples with one or more clumps can also include individual cells that are distinct from the clump(s). Thus, an isolated sample retrieved by infusing fluid into the duct and collecting the infused fluid mixed with the ductal fluid can provide multiple cells and one or more cell clumps for analysis. The advantage of cell clumps is that the clumping provides a framework for analysis of cell—cell interaction or a cell-to-cell relationship that in turn provides information about the status of the cells themselves. The invention provides the a ductal fluid sample comprising sufficient ductal epithelial cells from a breast duct for an analysis of the breast in which the duct is located. Insufficient ductal epithelial cells in a sample means that a cytological analysis of those cells can not be performed, or that the accuracy of the cytological analysis is compromised. The method of the invention and the composition provide samples from single breast ducts that can be analyzed because the samples so isolated contain sufficient material for an adequate analysis to be made. Ductal samples can comprise markers present in the fluid in addition to cells, i.e., molecules present in the cells collected and/or in the extracellular material retrieved from the breast duct. An advantage provided by the invention is that many more cells than have been previously collected are collectable and an accurate cytological analysis can therefore be made of the sample.

Relatively undisrupted cells and clumps can be analyzed to provide information on the cellular status in the breast duct from which the sample was collected. Further, collection of the ductal fluid from the breast duct provides enough cells and/or other material from the duct to provide a useful analysis of the condition of the breast. This is largely due to the fact that collection of the ductal fluid, cells and other material by infusing saline or other biocompatible wash fluid and collecting the wash fluid mixed with the ductal material results in collection of sufficient fluid and material for analysis. Suction may be applied to the lumen in the duct to facilitate collection of the ductal fluid and material once the duct has been filled with wash fluid (in order to prevent collapse of the ductal walls); reinfusion of wash fluid can follow in order to prevent collapse of the ductal walls and provide the opportunity for a second or subsequent intraductal aspiration and/or retrieval. Squeezing and massaging the breast may also be used in concert with infusion and collection procedures. The amount of material that is sufficient for analysis in a sample is at least one ductal epithelial clump up to at least 10 ductal epithelial clumps or more—each clump having from at least 4 to 6 ductal epithelial cells. For example, the sample from a non-discharging or discharging breast duct may have at least from 10 to 20 ductal epithelial cells, 20 to 50, 50 to 100, 100 to 1000, 1000 to 10,000, 10,000 to 50,000, or 50,000 to 100,000 ductal epithelial cells. The ductal epithelial cells may be present either individually or in clumps or both. Insufficient samples might include samples with less than 10 epithelial cells. An evaluation of insufficiency may be contingent on whether the cells are clumped or not.

The method of the invention is preparing a sample for use in diagnosis of breast cancer or pre-cancer comprising isolating a ductal fluid sample from one duct of a breast of a patient. The isolated ductal fluid is not mixed with ductal fluid from any other duct of the breast. The method can further include examining the isolated ductal fluid sample to determine the presence or absence of a marker. The duct from which the ductal fluid is isolated can be a duct that is not spontaneously discharging fluid. The marker for analysis can be selected from any known and useful markers for a breast condition, including pre-cancer and/or cancer markers, and further optionally including markers listed herein.

The isolated fluid sample can be examined to determine the presence of a marker. The presence of any marker, the absence of any marker, or the quality or state of any marker can be analyzed or examined. Particularly, the markers listed herein, and related forms or species of the markers listed herein are contemplated. The presence, absence or state of more than one marker can be examined. Markers can be examined in conjunction with ductal epithelial cell cytological analysis. The markers can be, for example, intracellular, nuclear, cytoplasmic, cell-surface, secreted, or extracellular markers. The markers can include any markers described in co-owned, co-pending, parent application Ser. No. 09/625,399 filed Jul. 26, 2000, application Ser. No. 09/502,404, filed on Feb. 10, 2000, and application Ser. No. 09/313,463, filed on May 17, 1999, hereby incorporated by reference in their entirety.

Examination of the ductal fluid for a marker can comprise determining absorption of a marker molecule by abnormal cells in the fluid. For example, absorption of iodide or a like molecule by cells in a ductal fluid sample can be measured. Examination of the ductal fluid for a marker can comprise analysis or examination of a quality and/or state of nucleic acid for such characteristic changes from the normal state as, for example, a loss of heterozygozity. Examination of the ductal fluid can comprise examining the fluid for the absence of a marker; especially where the marker is present in normal ductal fluid in a predetermined quantity in the population, and standards are set for benchmarks indicating a particular condition in the breast (ie., pre-cancer or cancer, or their various subcategories). Examination of the ductal fluid can comprise examining the ductal fluid for the presence or absence of two or more markers, including examining two or more markers for their state or quality, and including absorption of a marker, or loss of heterozygosity in the DNA of the cells retrieved from the isolated sample.

For example, the markers in this latter case can comprise DNA content, p53 gene or gene product, and G-actin or a nucleic acid encoding a polypeptide comprising at least a portion of G-actin. Thus, for example, examining the ductal fluid can comprise examining the fluid for the presence of at least one marker and the absence of at least one marker, e.g., examining the ductal fluid for the presence of an oncogene or its gene product, and examining the ductal fluid for the absence of a tumor suppressor molecule normally present in a given range or quantity in normal breast duct fluid or breast tissue. As an example, the ductal fluid can be examined for markers comprising such parameters as DNA content of the ductal epithelial cells, the absence or lowered levels of p53 gene or its gene product, and the presence of G-actin protein, polypeptide, or portion thereof, or a nucleic acid encoding a G-actin protein or polypeptide or portion thereof, e.g., as described in Rao et al, *Cancer Epid, Biomarkers & Prevention*, 1993 v. 7:1027–1033.

Preparing an isolated ductal fluid sample can comprise accessing the duct with a ductal access tool and collecting the ductal fluid sample while the tool remains in the duct. Having the tool remain in the duct for fluid infusion and fluid collection also ensures that the ductal fluid and ductal material collected are collected from a single duct not mixed with fluid or material from any other duct. Wash fluid infusion is used in the cases where the duct is not spontaneously discharging fluid so that the duct is filled or partially filled, the wash fluid mixes with ductal fluid and ductal contents, and retrieval of the mixed fluids comprises retrieval of a sample having sufficient cells and/or other markers for analysis of the condition of the duct from which the sample is taken. Previously the usefulness of ductal fluid retrieved by other means has been hampered by insufficient material or cells for analysis in the retrieved samples and/or not being able to identify the specific duct to which abnormal cells or other findings can be attributed. Since most breast cancers begin in a single, isolated, milk duct of a breast, the identification of a specific duct as abnormal (i.e., cancerous or pre-cancerous) is extremely useful, especially in concert with sufficient information from the isolated fluid sample in order to make a diagnosis. Collection of the isolated fluid sample can be facilitated by fluid infusion into the duct and collection of the wash fluid that has been infused mixed with ductal fluid and other ductal contents including ductal epithelial cells and other markers. The collection through the accessing lumen is facilitated after wash fluid infusion by a number of techniques that can be used together or separately and which are not limited to squeezing the breast, massaging the breast, applying negative pressure on the lumen to pull-up fluid into the lumen and/or collection receptacle, and using an additive in the wash fluid that delays or inhibits absorption of the fluid into the ductal walls (thereby keeping more fluid in the duct to be retrieved). Many of these techniques and tools for practicing these techniques are described in co-owned U.S. Ser. No. 09/067,661, U.S. Ser. No. 09/301,058, PCT US99/09141, U.S. Ser. No. 09/313,463, U.S. Ser. No. 09/473,510, PCT US99/31086 herein incorporated by reference in their entirety.

By the procedure of ductal lavage, ductal epithelial cells that line the walls of the ductal lumen are washed out of the duct. Lavage or wash fluid is infused into the duct, and the lavage fluid mixed with ductal fluid is collected. Lavage is described in copending and co-owned applications including Ser. No. 09/067,661, 09/301,058, PCT US99/09141, 60/122, 076, 09/313,463, 60/143,359, and U.S. Ser. No. 09/473,510, all incorporated by reference in their entirety. Suction can be applied to the tool accessing the ductal lumen in order to retrieve a maximum amount of cells and/or fluid. Lavage or wash fluid can be infused into the duct, and collected. Suction can be applied to the tool accessing the ductal lumen in order to retrieve a maximum amount of cells and/or fluid. The duct can be flushed by infusing saline into the duct until resistance is met, applying pressure and/or squeezing the breast, e.g., particularly at the base of the breast, and capturing the fluid that moves up through the duct after the pressure is applied. Flushing can continue by infusing more saline and applying more pressure.

In order to retrieve cells and ductal material sufficient for analysis of a single non-discharging breast duct and a corresponding diagnosis, a non-discharging duct can be accessed by a tool capable of infusing wash fluid and also capable of collecting the ductal fluid mixed with wash fluid while the tool remains in the duct as described herein. Thus, ductal fluid can be retrieved by a medical tool, e.g., a catheter or a cannula, placed into the duct to infuse wash fluid to retrieve a mixture of wash fluid and ductal fluid from the duct without removal of the tool. Thus, by the method of the invention, the tool remains indwelling while wash fluid is infused and wash fluid mixed with ductal fluid (comprising cells and cellular material, etc.) is collected. The fluid from the breast duct can contain ductal epithelial cells, including cells of a stage considered to be pre-cancerous or cancerous as described, and may also contain various molecules either connected to the cells or separate from them that may be used as markers. Either presence or absence or decrease or increase relative to a normal or benign control amount can indicate cancer or pre-cancer.

The method is practiced by providing a ductal fluid sample from at least one duct of a breast of the patient. Providing the ductal fluid sample can be accomplished by obtaining the sample from the breast or by receiving a sample that had been previously obtained. For example, a laboratory can receive a ductal fluid sample from a patient or a practitioner, and the laboratory can be directed to make an analysis of the sample. The isolated fluid is collected by some available technique including, for example, ductal lavage of a single duct. In general, collection of isolated ductal fluid not mixed with ductal fluid from another duct of the breast can be accomplished by accessing the duct with a breast duct access tool that infuses fluid and collects ductal fluid mixed with the infused fluid, while the tool remains in the duct. Also, the collection tube can be marked and the duct can be marked so that the analysis of the fluid is traceable to one duct which can be re-identified and re-accessed if appropriate.

The marker may be a nucleic acid or protein form of the marker. For example, the marker may be "X", and either a nucleic acid sequence encoding at least a portion of X, or a gene product at least a portion of protein or polypeptide X can be determined or measured. The marker may also be a non-nucleic acid or a non-amino acid molecule, such as, for example, a small organic molecule, a lipid, a fat, a biologically formed organic acid or base, a carbohydrate or other sugar type molecule, a polymer type molecule or a portion of such molecule, a moiety that characterizes a marker, for example a side chain on a marker, etc.

Thus, for example, the method of providing an isolated ductal fluid sample, and examining the sample for one or more markers can comprise examining the sample for the presence, absence, or relative level of any one or more of the following markers:

1. lysophosphatidic acid (LPA) or a lysophospholipid, or a receptor of lysophosphatidic acid, e.g., as described in Goetzl et al, Cancer Res Sep. 15, 1999 v.59: 4732–7, Xu et al, Biochem J 1995 v.309: 933–40, and Contos et al, Mol Pharmacol 2000 v.58: 1188–1196;
2. palladin, a portion of palladin, or a nucleic acid encoding a polypeptide comprising at least a portion of paladin, e.g., as described in Reuters Health News Aug. 7, 2000, and Parast and Otey, J Cell Biol Aug. 7, 2000 v. 150:643–56;

3. Lg, a portion of Lg, or a nucleic acid encoding a polypeptide comprising at least a portion of Lg, e.g., as described in Ranganathan et al, J Steroid Biochem Mol Biol 1999 v.70: 151–8;
4. E2F1, a portion of E2F1, or a nucleic acid encoding a polypeptide comprising at least a portion of E2F1, e.g., as described in Klein-Szanto et al Cancer Epid Biomarkers & Prevention 2000 v. 9: 395–401;
5. T1A12/mac 25, a portion of T1A12/mac 25, or a nucleic acid encoding a polypeptide comprising at least a portion of T1A 12/mac 25, e.g., as described in Burger et al Oncogene 1998 v. 16:2459–67;
6. MAGUK/ZO-1, a portion of MAGUK/ZO-1, a nucleic acid encoding a polypeptide comprising at least a portion of MAGUK/ZO-1, e.g., as described in Hoover et al, Am J Pathol 1998 v.153: 1767–73;
7. Repressor of estrogen receptor activity (REA), a portion of REA, a nucleic acid encoding a polypeptide comprising at least a portion of REA, e.g., as described in Simon et al, Cancer Res 2000 v. 60:2796–9;
8. prothymosin alpha (PTA), a portion of PTA, a nucleic acid encoding a polypeptide comprising at least a portion of PTA, e.g., as described in Domineguez et al, Br J of Cancer 2000 v. 82:584–590; and Magdalena et al, Br J Cancer 2000 v. 82:584–590;
9. TNF-related apoptosis-inducing ligand (TRAIL), a nucleic acid encoding a polypeptide comprising at least a portion of TRAIL, e.g., as described in Griffith et al, J Immunol 2000 v. 165:2886–94; and Herrnring et al Histochem Cell Biol 2000 v. 113:189–94;
10. BU101 protein, a nucleic acid encoding a polypeptide comprising at least a portion of BU101, e.g., as described in WO 98/07857;
11. c-raf kinase, a portion of c-raf kinase, a nucleic acid encoding a polypeptide comprising at least a portion of c-raf kinase, e.g., as described in El-Ashry et al, Oncogene 1997 v.15: 423–35, and Callans et al, Ann Surg. Oncol 1995 v.2: 38–42;
12. CD66a, a portion of CD66a, a nucleic acid encoding a polypeptide comprising at least a portion of CD66a, e.g., as described in Huang et al Anticancer Res. 1998 v.18: 3203–12;
13. KL-1, a portion of KL-1, a nucleic acid encoding a polypeptide comprising at least a portion of KL-1, e.g., as described in Okumura et al, Jpn J Clin Oncol 1998 v.28: 480–5;
14. cell adhesion molecule 5.2 (CAM 5.2), a portion of CAM 5.2, a nucleic acid encoding a polypeptide comprising at least a portion of CAM 5.2, e.g., as described in Okumura et al, Jpn J Clin Oncol 1998 v.28: 480–5;
15. leptin, a portion of leptin, a nucleic acid encoding a polypeptide comprising at least a portion of leptin, e.g., as described in Tessitore et al, Int J Mol Med 2000 v.5: 421–6;
16. Bcl-2 gene product, at least a portion of Bcl-2 gene product or polypeptide, a nucleic acid encoding a polypeptide encoding at least a portion of Bcl-2 gene product, e.g., as described in Krajewski et al Endocr Relat Cancer 1999 v.6: 29–40, and Castiglione et al Anticancer Res. 1999 v. 19:4555–63, Simony-Lafontaine et al, 2000 v.82: 1958–66;
17. nuclear matrix 23(nm23), a portion of nm23, a nucleic acid encoding a polypeptide comprising at least a portion of nm23, e.g., as described in Vazquez-Ramirez et al, Pathol Res Pract 2000 v.196: 553–9, Cipollini et al, Cancer Genet Cytogenet 2000 v. 121:181–5;
18. an apotosis-related protein, a portion of said protein, a nucleic acid encoding a polypeptide comprising at least a portion of the apoptosis-related protein, e.g., as described in Dowsett et al, Endocr Relat Cancer 1999 v.6: 25–8;
19. lipocalin NGAL, a portion of lipocalin NGAL, a nucleic acid encoding a polypeptide comprising at least a portion of lipocalin NGAL, e.g., as described in Stoesz et al, Int J Cancer 1998 v.79: 565–72;
20. thymosin beta-15, a portion of thymosin beta-15, a nucleic acid encoding a polypeptide comprising at least a portion of thymosin bet15, e.g., as described in U.S. Pat. No. 5,663,071 and WO 97/48805;
21. tumor amplified kinase STK15 (also BTAK and aurora2), at least a portion of STK15, a nucleic acid encoding at least a portion of STK15; e.g., as described in Zhou et al, Nat Genet 1998 v. 20:189–93;
22. complement regulatory protein CD 46, a portion of CD46, a nucleic acid encoding at least a portion of CD46; as described e.g., in Thorsteinsson et al APMIS 1998 v. 106:869–78;
23. complement regulatory protein CD 59, a portion of CD 59, a nucleic acid encoding at least a portion of CD59; as described e.g., in Thorsteinsson et al APMIS 1998 v. 106:869–78;
24. a nucleic acid encoding a portion of an FHIT gene, e.g., as described in Huiping et al, Eur J Cancer 2000 v.36: 1552–7, Gatalica et al, Cancer 2000 v.88: 1378–83, Ahmadian et al, Cancer Res 1997 v. 57:3664–8, and Campiglio et al, Cancer Res 1999 v. 59:3866–9;
25. loss of heterozygosity (LOH), e.g., as described in Linginger et al, Mod Pathol 1998 v. 11:1151–9; and Larson et al, Am J Pathol 1998 v. 152:1591–8;
26. LOH at an FRA3B site, e.g., as described in Ahmadian et al, Cancer Res 1997 v. 57:3664–8;
27. MRP-1/CD9, a portion of MRP-1/CD9, a nucleic acid encoding at least a portion of MRP-1/CD9, e.g., as described in van den Heuvel-Eibrink et al, Int J Clin Pharmacol Ther 2000 v. 38:94–110, Huang et al Am J Pathol 1998 v.153: 973–83, Miyake et al Cancer Res 1996 v. 56:1244–9, and Miyake et al Cancer Res. 1995 v.55: 4127–31;
28. KAI1/CD82, a portion of KAI1/CD82, a nucleic acid encoding at least a portion of KAI1/CD82, e.g., as described in Huang et al Am J Pathol 1998 v.153: 973–83;
29. TMS-1, a portion of TMS-1, a nucleic acid encoding a polypeptide comprising at least a portion of TMS-1, for example as described in McConnell and Vertino, Cancer Res. Nov. 15, 2000;60(22):6243–7; Conway et al, Cancer Res Nov. 15, 2000;60(22):6236–42; and Grossman et al, J Exp Biol 2000 v.203: 447–57;
30. at least a portion of breast cancer associated gene (BRCA), e.g., as described in Seances et al, Soc. Biol Fil 1998 v. 192:35–40, and Deng and Brodie, Bioessays 2000 v.22: 728–37;
31. absorption of a marker (e.g., iodide), e.g., as described in De La Vieja et al, Physiol Rev 2000 v.80: 1083–105, Tazebay et al, Nat Med 2000 v. 6:871–8;
32. Fibroblast growth factor (FGF) protein, a portion of an FGF protein or polypeptide, a nucleic acid encoding at least a portion of an FGF protein or polypeptide, e.g., as described in Fernig et al, Cancer Treat Res 1991 v.53: 47–78, and De Benedetti and Harris, Int J Biochem Cell Biol 1999 v.31: 59–72;

33. Vascular endothelial growth factor (VEGF) protein, a portion of a VEGF protein or polypeptide, a nucleic acid encoding at least a portion of a VEGF protein or polypeptide e.g, as described in Gasparini, Oncologist 2000; 5 suppl 1:37–44;

34. Insulin-like growth factor-1 (IGF-1 protein, a portion of an IGF-1 protein or polypeptide, a nucleic acid encoding at least a portion of an IGF-1 protein or polypeptide e.g., as described in Pollack, Eur J Cancer 2000 v. 36:1224–8;

35. Maspin protein, a portion of a maspin protein or polypeptide, a nucleic acid encoding at least a portion of a maspin protein or polypeptide, e.g., as described in Sager et al, Adv Exp Med Biol 1997 v.425: 77–88.

36. CDw60 protein, a portion of CDw60 protein or polypeptide, a nucleic acid encoding at least a portion of a CDw60 protein or polypeptide, e.g., as described in Gocht et al, Histochem J 2000 Jul;32(7):447–56.

37. Mammary expressed enzymes (e.g., cytochrome P450s, catechol-Omethyltransferase, epoxide hydrolase, peroxidases, glutathione Stransferases, N-acetyltransferases, and sulfotransferases) a nucleic acid encoding at least a portion of a mammary expressed enzyme, e.g., as described in Williams and Phillips, *Cancer Res* Sep. 1, 2000:60(17):4667–77.

38. Mammastatin protein or polypeptide (47 kD and/or 65 kD), a nucleic acid encoding at least a portion of a mammastatin protein or polypeptide, e.g., as described in Ervin et al, *Science* 1989; 244(4912); 1585–7.

39. Kallikrein 6 (zyme/protease M/neurosin) protein or polypeptide (hK6), a nucleic acid encoding at least a portion of an hK6 protein or polypeptide, e.g., as described in Diamandis et al, Clin Biochem 2000 Oct;33(7):579–583; Diamandis et al, Clin Biochem 2000 Jul;33(5):369–75; Yousef et al, Genomics Nov. 1, 2000;69(3):331–41.

As discussed, the cells collected can comprise ductal epithelial cells and the ductal fluid collected can comprise molecular and cellular material. The collected cells and fluid and fluid components can be analyzed, e.g., as described or suggested herein. Fluid collected from the milk ducts, can include constituents of biological fluids, e.g., those typically found in breast duct fluid, e.g., water, cells, cellular markers, molecular markers, nucleic acids, proteins, cellular debris, salts, particles or organic molecules. These constituents can be analyzed by any appropriate method depending on the marker and the diagnostic purpose. In addition, any of the cells of the duct can be analyzed for morphological abnormalities in cell components, including, e.g., morphological abnormalities of the nucleus, cytoplasm, Golgi apparatus or other parts of a cell. Cell morphology can serve to establish whether the ductal epithelial cells are normal (i.e., not pre-cancerous or cancerous or having another noncancerous abnormality), pre-cancerous (i.e., comprising hyperplasia, atypical ductal hyperplasia (ADH) or low grade ductal carcinoma in situ (LG-DCIS)) or cancerous (i.e., comprising high grade ductal carcinoma in situ (HG-DCIS), or invasive carcinoma). Analysis of cell contents may serve to establish similar staging as established by morphology, capturing generally a progression of a pre-cancerous or cancerous condition in the cells.

Once the ductal fluid sample is retrieved from the breast it is examined for the presence of a marker such as, for example a protein, a polypeptide, a peptide, a nucleic acid, a polynucleotide, an mRNA, a small organic molecule, a lipid, a fat, a glycoprotein, a glycopeptide, a carbohydrate, an oligosaccharide, and a chromosomal abnormality, a whole cell having a marker molecule, a particle, a secreted molecule, an intracellular molecule, and a complex of a plurality of molecules as described above. In addition, the marker may be capable of distinguishing between any two cytological categories consisting of normal, abnormal, hyperplasia, atypia, ductal carcinoma, ductal carcinoma in situ (DCIS), ductal carcinoma in situ—low grade (DCIS-LG), ductal carcinoma in situ high grade (DCIS-HG), invasive carcinoma, atypical mild changes, atypical marked changes, atypical ductal hyperplasia (ADH), insufficient cellular material for diagnosis, and sufficient cellular material for diagnosis. These categories classify the epithelial cells cytologically, and these classifications may indicate either cancer or its precursors, or absence of cancer indicia.

Analysis of cell contents may serve to establish similar staging as established by morphology, capturing generally a progression of a pre-cancerous or cancerous condition in the cells. Thus the ductal epithelial cells may be analyzed for other markers, e.g., protein markers, nucleic acid markers, particles, complexes, or biochemical or molecular markers in the cells or on the cell surfaces or secreted by the cell or for any marker providing evidence of neoplasia. The ductal epithelial cell can be derived from any part of the breast milk duct, including, e.g., the ductal lumen and/or the terminal ductal lobular unit (TDLU). Cells derived from the TDLU may also have similar stages as found in other lumenal ductal epithelial cells not from the TDLU including, e.g., hyperplasia, atypia, in situ carcinoma, and invasive carcinoma.

Once the wash fluid has been infused in the duct and the wash fluid and ductal fluid is collected from a breast duct, the cellular material can be separated and can be examined. The cellular material can include, e.g., substances selected from the group consisting of whole cells, cellular debris, proteins, nucleic acids, polypeptides, glycoproteins, lipids, fats, glycoproteins, small organic molecules, metabolites, and macromolecules. These materials may be found in the cell, on the cell surface or as material secreted from the cell and found in fluid outside the cell. These materials may be synthesized by a cell, or may be otherwise present in the fluid from the duct, e.g., as by-products or degradation products of molecules in the body. Cytology, or any other suitable method for analyzing the condition of the cells can be used to examine whole cells. Other markers present in the cellular material, ductal fluid, or other material obtained from the breast duct can be analyzed as is appropriate for the marker being sought, including e.g., binding assays, immunohistochemistry, or using other analytical techniques for distinguishing and identifying biological molecules obtained from biological material. Examining the ductal fluid sample can also be performed to determine the presence of a marker comprising, for example, a protein, a polypeptide, a peptide, a nucleic acid, a polynucleotide, an mRNA, a small organic molecule, a lipid, a fat, a glycoprotein, a glycopeptide, a carbohydrate, an oligosaccharide, a chromosomal abnormality, a whole cell having a marker molecule, a particle, a secreted molecule, an intracellular molecule, or a complex of a plurality of molecules. Detection and analysis of these classifications of markers can be accomplished, for example, using standard assays for determining the presence of a particular marker or marker classification and/or for example as described in Sambrook et al., Molecular Cloning: A Laboratory Manual, $2^{nd}$ Ed. (Cold Spring Harbor Press, Cold Spring Harbor, N.Y. 1989).

Examining the ductal fluid sample can comprise determining the presence of a marker comprising RNA, DNA, protein, polypeptide, or peptide form of a marker such as lysophosphatidic acid, a lysophospholipid, paladin, a portion of palladin, a nucleic acid encoding a polypeptide comprising at least a portion of paladin, Lg, a portion of Lg, a nucleic acid encoding a polypeptide comprising at least a portion of Lg, E2F1, a portion of E2F1, a nucleic acid encoding a polypeptide comprising at least a portion of E2F1, T1A12/mac 25, a portion of T1A12/mac 25, a nucleic acid encoding a polypeptide comprising at least a portion of T1A12/mac 25, MAGUK/ZO-1, a portion of MAGUK/ZO-1, a nucleic acid encoding a polypeptide comprising at least a portion of MAGUK/ZO-1, repressor of estrogen receptor activity (REA), a portion of REA, a nucleic acid encoding a polypeptide comprising at least a portion of REA, prothymosin alpha (PTA), a portion of PTA, a nucleic acid encoding a polypeptide comprising at least a portion of PTA, c-raf kinase, a portion of c-raf kinase, a nucleic acid encoding a polypeptide comprising at least a portion of c-raf kinase, CD66a, a portion of CD66a, a nucleic acid encoding a polypeptide comprising at least a portion of CD66a, KL-1, a portion of KL-1, a nucleic acid encoding a polypeptide comprising at least a portion of KL-1, cell adhesion molecule 5.2 (CAM 5.2), a portion of CAM 5.2, a nucleic acid encoding a polypeptide comprising at least a portion of CAM 5.2, leptin, a portion of leptin, a nucleic acid encoding a polypeptide comprising at least a portion of leptin, Bcl-2 gene product, at least a portion of Bcl-2 gene product or polypeptide, a nucleic acid encoding a polypeptide encoding at least a portion of Bcl-2 gene product, nuclear matrix 23(nm23), a portion of nm23, a nucleic acid encoding a polypeptide comprising at least a portion of nm23, an apotosis-related protein, a portion of said protein, a nucleic acid encoding a polypeptide comprising at least a portion of the apoptosis-related protein, comprises lipocalin NGAL, a portion of lipocalin NGAL, a nucleic acid encoding a polypeptide comprising at least a portion of lipocalin NGAL, a nucleic acid encoding a portion of an FHIT gene, loss of heterozygosity at an FRA3B site, MRP-1/CD9, a portion of MRP-1/CD9, a nucleic acid encoding at least a portion of MRP-1/CD9, KAI1/CD82, a portion of KAI1/CD82, a nucleic acid encoding at least a portion of KAI1/CD82, at least a portion of breast cancer associated gene, TMS-1, a portion of TMS-1, a nucleic acid encoding a polypeptide comprising at least a portion of TMS-1; at least a portion of breast cancer associated gene (BRCA); absorption of a marker (e.g., iodide). fibroblast growth factor (FGF) protein, a portion of an FGF protein or polypeptide, a nucleic acid encoding at least a portion of an FGF protein or polypeptide, vascular endothelial growth factor (VEGF) protein, a portion of a VEGF protein or polypeptide, a nucleic acid encoding at least a portion of a VEGF protein or polypeptide, insulin-like growth factor-1 (IGF-1 protein, a portion of an IGF-1 protein or polypeptide, a nucleic acid encoding at least a portion of an IGF-1 protein or polypeptide; maspin protein, a portion of a maspin protein or polypeptide, a nucleic acid encoding at least a portion of a maspin protein or polypeptide, CDw60 protein, a portion of CDw60 protein or polypeptide, a nucleic acid encoding at least a portion of a CDw60 protein or polypeptide, mammary expressed enzymes (e.g., cytochrome P450s, catechol-O-methyltransferase, epoxide hydrolase, peroxidases, glutathione S-transferases, N-acetyltransferases, and sulfotransferases) a nucleic acid encoding at least a portion of a mammary expressed enzyme, mammastatin protein or polypeptide (47 kD and/or 65 kD), a nucleic acid encoding at least a portion of mammastatin protein or polypeptide; kallikrein 6 (zyme/protease M/neurosin) protein or polypeptide (hK6), and a nucleic encoding at least a portion of an hK6 protein or polypeptide.

A level of the marker can be a presence relative to a normal control or an absence relative to a normal control of a given marker. Increased or decreased amounts relative to such normal controls can also be determined. The normal control can be determined relative to the particular patient, or relative to a patient population. In addition, the quality of the marker can be assessed. A quality of a marker can be such changes as DNA mutation, or a quantity of mutations, a deterioration of chromosomal quality or quantity, degradation of a protein, or a change in quantity of a nucleic acid or chromosome. A quality can be an erosion of a molecule, particle, molecule or organelle with respect to a normal quality. A tumor suppressor, e.g., mammastatin may be used as a marker where a reduction in the marker identifies a cancerous or pre-cancerous condition in the breast.

Chromosomal abnormalities in ductal epithelial cells can also provide information and act as a marker to identify cancer or pre-cancer as described in Mark et al (1999) *Cancer Genet Cytogenet* 108:26–31; Lundlin and Mertens (1998) *Breast Cancer Res Treat* 51:1–15; Newsham (1998) *Am J Pathol* 153:5–9; Larson etal (1998) *Am J Pathol* 152:1591–8; Adelaide et al (1998) *Genes Chromosomes Cancer* 22:186–99; Fejzo et al (1998) *Gene Chromosome Cancer* 22:105–113; Dietrich et al (1998) *Hum Pathol* 12: 1379–82; Cavalli et al (1997) Hereditas 126:261–8; Adeyinka et al (1997) *Cancer Genet Cytogenet* 97:119–21; Afify and Mark (1997) *Cancer Genet Cytogenet* 97:101–5; Brenner and Aldaz (1997) *Prog Clin Biol Res* 396: 63–82; Mark et al (1997) *Ann Clin Lab Sci* 27:47–56; and Fabian et al 1993 *J. Cellular Biochemistry* 17G:153–16.

Standard assay procedures for identifying the markers can be used, including antibodies or other binding partners, labels, stains, pattern analysis (for cells and cell components), and in general any other chemical or visual identification techniques.

The different categories of markers are tested differently depending on the category and possibly also on the location of the marker in the cell (for example, a cell surface protein might be detected differently than a cytoplasmic or nuclear protein). Typically, assays comprising one or more of binding, coloration, precipitation, affinity column selection, in-situ binding, solution phase binding, nucleic acid probe labeling, protein probe labeling, polypeptide probe labeling, peptide probe labeling, and/or a combination or variation of these processes can be used. Standard procedures for conducting such assays generally (e.g., ELISA, RNA or DNA probe hybridization, and other binding or other detection assays) are described in Sambrook et al., Molecular Cloning: A Laboratory Manual, $2^{nd}$ Ed. (Cold Spring Harbor Press, Cold Spring Harbor, N.Y. 1989). Standard assay procedures for identifying the markers can be used, including antibodies or other binding partners, labels, stains, pattern analysis (for cells and cell components), and in general any other chemical or visual identification techniques.

In general, markers can be categorized nonexclusively, and often in overlapping categories, for example, protein expression, mRNA expression, post-translational change in a protein and/or DNA change in a gene may all be used in concert or separately for the same or a plurality of markers to make a diagnosis.

Cytology, or any other suitable method for analyzing the condition of the cells can be used to examine whole cells. Markers present in the cellular material, ductal fluid generally, or other material obtained from the breast duct can be analyzed as is appropriate for the marker being sought, including, e.g., binding assays, immunohistochemistry, or using other analytical techniques for distinguishing and identifying biological molecules obtained from biological material.

Once the ductal fluid is analyzed for one or more markers, the fluid may also be analyzed cytologically to determine the cytological status of the ductal epithelial cells and other cells. Cytological assays that can be performed on the cells retrieved from a duct or from nipple aspirate can include e.g., assays described in King et al, *J. Nat'l Cancer Inst* (1983) 71:1115–21, Wrensch et al. (1992) *Am. J. Epidem.* 135: 130–141, Papanicolaou et al, (1958) *Cancer,* 11:377–409 and Goodson WH & King EB, *Chapter 4: Discharges and Secretions of the Nipple,* THE BREAST: COMPREHENSIVE MANAGEMENT OF BENIGN AND MALIGNANT DISEASES (1998) $2^{nd}$ Ed. vol 2, Bland & Kirby eds. W.B. Saunders Co, Philadelphia, Pa. pp. 51–74. For example, as described in Goodson and King (page 60) atypical hyperplasia presents as having cellular abnormalities, increased coarseness of the chromatin, and tendency for more single cells as well as groups of cells. With regard to carcinoma in situ, Papanicolaou et al described cellular abnormalities, e.g., nuclear abnormalities diagnosed by cytology of fluid from nipple secretions containing ductal cells. The cytological examination of abnormal cells can also be conducted as described in Sartorius et al (1977) *J. Natl Cancer Inst* 59: 1073–1080. and King et al, (1983) *JNCI* 71(6) 1115–1121. Atypia and carcinoma in situ are widely characterized pathologically, as described in Page et al, (1998) *Mod Pathol* 11(2): 120–8. The ductal fluid can be analyzed by cytological techniques by placing some of the fluid on a slide with a standard cytological stain and observing under a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline TS and IK, Pub Igaku-Shoin Medical ""Breast: Guides to Clinical Aspiration Biopsy" (LSBN 0896401596; Masood, American *Society of Clinical Pathology:* November 199S, "Cytopathology of the Breast" ISBN 0891893806; and Feldman PS, *American Society of Clinical Pathology,* November 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, (Can FNA biopsy separate atypical hyperplasia, carcinoma in situ, and invasive carcinoma of the breast? Cytomorphologic criteria and limitations in diagnosis, Diagnostic Cytopathology) 9(6): 713–28, 1993; Masood et al, (Immunohistochemical differentiation of atypical hyperplasia vs. carcinoma in situ of the breast) *Cancer Detection & Prevention.* 16(4): 225–35, 1992; Masood et al, (Cytologic differentiation between proliferative and nonproliferative breast disease in mammographically guided fine-needle aspirates) *Diagnostic Cytopathology.* 7 (6): 581–90, 1991; Masood S., (Occult breast lesions and aspiration biopsy: a new challenge) *Diagnostic Cytopathology.* 9(6): 613–4, 1993; Masood S., (Prognostic factors in breast cancer: use of cytologic preparations) *Diagnostic Cytopathology.* 13(5): 388–95, 1995, Novak and Masood, (Nuclear grooves in fine-needle aspiration biopsies of breast lesions: do they have any significance?) *Diagnostic Cytopathology.* 18(5): 333–7, 1998; Sidawy et al, (Interobserver variability in the classification of proliferative breast lesions by fine-needle aspiration: results of the Papanicolaou Society of Cytopathology Study) *Diagnostic Cytopathology.* 18(2): 15065, 1998; Masood et al, (Automation in cytology: a survey conducted by the New Technology Task Force, Papanicolaou Society of Cytopathology) *Diagnostic Cytopathology.* 18(1): 47–55, 1998; and Frykberg and Masood Copeland EM 3d. Bland KI., (Ductal carcinoma in situ of the breast) *Surgery, Gynecology & Obstetrics* 177(4): 425–40, 1993.

The invention also provides systems for preparing a sample for use in diagnosis of breast cancer or pre-cancer, the system comprising a tool to retrieve ductal fluid from a breast duct and instructions for use to isolate a ductal fluid sample from a duct, particularly a non-spontaneously discharging breast duct in order to determine the presence of one or more markers. Materials and instructions may also be included in the system to determine the presence or absence of a marker in the isolated ductal fluid. Materials may be included to make a cytodiagnosis of collected ductal epithelial cells. A cytological reading of the ductal epithelial cells collected with the infused wash fluid is one type of marker which can be used for diagnosing a condition in a breast duct. Instructions in the kit or system can include guidance for interpreting cytological data and/or other marker data in order to make a diagnosis. The systems or kits may include a ductal access tool, for example in order to retrieve the ductal fluid, e.g., especially where it is preferred that the ductal fluid be identified as coming from a specific duct (so that the duct can be accessed later for treatment and/or further monitoring). Methods for identifying the non-spontaneously discharging duct may also be included in the system or kit. The instructions in the systems or kits can include directions according to the methods of identifying breast cancer or pre-cancer described herein, and possibly including any marker or markers or marker classification group or groups that could be useful and/or are described herein. The system or kit can include assay reagents for detecting the marker or markers. The system or kit may comprise a panel of reagents for detecting a plurality of markers either simultaneously or sequentially, or some other practical combination of testing modalities. The system or kit can also include indexes and parameters for making a diagnosis, depending on the marker or markers. The system or kit can include a container for the contents of the system or kit.

EXAMPLES

Retrieval of Ductal Fluid and Analysis of Markers in the Fluid

A patient is prepared for a ductal access procedure. Using a ductal access tool, a duct on each breast is infused with sufficient wash fluid, and the wash fluid mixed with ductal fluid is collected separately from each accessed duct. The fluid in each duct that is accessed is analyzed for the presence, absence or relative levels (as compared to a predetermined normal level) of one or more of the following markers using standard techniques: lysophosphatidic acid, a lysophospholipid, paladin, a portion of palladin, a nucleic acid encoding a polypeptide comprising at least a portion of paladin, Lg, a portion of Lg, a nucleic acid encoding a polypeptide comprising at least a portion of Lg, E2F1, a portion of E2F1, a nucleic acid encoding a polypeptide comprising at least a portion of E2F1, T1A12/mac 25, a portion of T1A12/mac 25, a nucleic acid encoding a polypeptide comprising at least a portion of T1A12/mac 25, MAGUK/ZO-1, a portion of MAGUK/ZO-1, a nucleic acid encoding a polypeptide comprising at least a portion of MAGUK/ZO-1, repressor of estrogen receptor activity (REA), a portion of REA, a nucleic acid encoding a polypeptide comprising at least a portion of REA, prothymosin alpha (PTA), a portion of PTA, a nucleic acid encoding a polypeptide comprising at least a portion of PTA, TNF-related apoptosis-inducing ligand (TRAIL), a nucleic acid encoding a polypeptide comprising at least a portion of TRAIL, BU101 protein, a nucleic acid encoding a polypeptide comprising at least a portion of BU101, c-raf kinase, a portion of c-raf kinase, a nucleic acid encoding a polypeptide comprising at least a portion of c-raf kinase, CD66a, a portion of CD66a, a nucleic acid encoding a polypeptide comprising at least a portion of CD66a, KL-1, a portion of KL-1, a nucleic acid encoding a polypeptide comprising at least a portion of KL-1, cell adhesion molecule 5.2 (CAM 5.2), a portion of CAM 5.2, a nucleic acid encoding a polypeptide comprising at least a portion of CAM 5.2, leptin, a portion of leptin, a nucleic acid encoding a polypeptide comprising at least a portion of leptin, Bcl-2 gene product, at least a portion of Bcl-2 gene product or polypeptide, a nucleic acid encoding a polypeptide encoding at least a portion of Bcl-2 gene product, nuclear matrix 23(nm23), a portion of nm23, a nucleic acid encoding a polypeptide comprising at least a portion of nm23, an apotosis-related protein, a portion of said protein, a nucleic acid encoding a polypeptide comprising at least a portion of the apoptosis-related protein, comprises lipocalin NGAL, a portion of lipocalin NGAL, a nucleic acid encoding a polypeptide comprising at least a portion of lipocalin NGAL, thymosin beta-15, a portion of thymosin beta-15, a nucleic acid encoding a polypeptide comprising at least a portion of thymosin beta-15, a nucleic acid encoding a portion of an FHIT gene, loss of heterozygosity at an FRA3B site, MRP-1/CD9, a portion of MRP-1/CD9, a nucleic acid encoding at least a portion of MRP-1/CD9, KAI1/CD82, a portion of KAI1/CD82, a nucleic acid encoding at least a portion of KAI1/CD82, at least a portion of breast cancer associated gene, TMS-1, a portion of TMS-1, a nucleic acid encoding a polypeptide comprising at least a portion of TMS-1; at least a portion of breast cancer associated gene (BRCA); absorption of a marker (e.g., iodide). fibroblast growth factor (FGF) protein, a portion of an FGF protein or polypeptide, a nucleic acid encoding at least a portion of an FGF protein or polypeptide, vascular endothelial growth factor (VEGF) protein, a portion of a VEGF protein or polypeptide, a nucleic acid encoding at least a portion of a VEGF protein or polypeptide, insulin-like growth factor-1 (IGF-1 protein, a portion of an IGF-1 protein or polypeptide, a nucleic acid encoding at least a portion of an IGF-1 protein or polypeptide; maspin protein, a portion of a maspin protein or polypeptide, a nucleic acid encoding at least a portion of a maspin protein or polypeptide, CDw60 protein, a portion of CDw60 protein or polypeptide, a nucleic acid encoding at least a portion of a CDw60 protein or polypeptide, mammary expressed enzymes (e.g., cytochrome P450s, catechol-O-methyltransferase, epoxide hydrolase, peroxidases, glutathione S-transferases, N-acetyltransferases, and sulfotransferases) a nucleic acid encoding at least a portion of a mammary expressed enzyme, mammastatin protein or polypeptide (e.g., 47 kD and/or 65 kD), a nucleic acid encoding a mammastatin protein or polypeptide; kallikrein 6 (zyme/protease Mineurosin) protein or polypeptide (hK6), and a nucleic acid encoding at least a portion of an hK6 protein or polypeptide. Cytodiagnosis of a sample of the collected ductal epithelial cells, as individual cells and as cells in clumps is also made to support any other marker data from the collected fluid and material.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method to aid in diagnosing breast cancer or pre-cancer comprising:
    placing a ductal access tool comprising a single lumen in a breast duct of a patient, wherein the single lumen has an inner diameter large enough to retrieve clusters of greater than 10 cells;
    infusing a fluid into the duct through the single lumen; and
    retrieving a ductal fluid sample from the accessed duct through the single lumen, wherein the ductal fluid sample comprises ductal epithelial cells and is free of ductal fluid from any other duct of the breast.

2. A method as in claim 1, further comprising:
    examining the ductal fluid sample to determine the presence or absence of a marker.

3. A method a in claim 1, wherein the duct from which the ductal fluid sample is retrieved is not spontaneously discharging ductal fluid.

4. A method as in claim 2, wherein the marker is selected from the group consisting of: lysophosphatidic acid, a lysophospholipid, palladin, a portion of palladin, a nucleic acid encoding a polypeptide comprising at least a portion of palladin Lg, a portion of Lg, a nucleic acid encoding a polypeptide comprising at least a portion of Lg, E2F1, a portion of E2F 1, a nucleic acid encoding a polypeptide comprising at least a portion of E2F1, T1A12/mac 25, a portion of T1A12/mac 25, a nucleic acid encoding a polypeptide comprising at least a portion of T1A12/mac 25, MAGUK/ZO-1, a portion of MAGUK/ZO-1, a nucleic acid encoding a polypeptide comprising at least a portion of MAGUK/ZO-1, repressor of estrogen receptor activity (REA), a portion of REA, a nucleic acid encoding a polypeptide comprising at least a portion of REA, prothymosin alpha (PTA), a portion of PTA, a nucleic acid encoding a polypeptide comprising at least a portion of PTA, c-raf kinase, a portion of c-raf kinase, a nucleic acid encoding a polypeptide comprising at least a portion of c-raf kinase, CD66a, a portion of CD66a, a nucleic acid encoding a polypeptide comprising at least a portion of CD66a, KL-1, a portion of KL-1, a nucleic acid encoding a polypeptide comprising at least a portion of KL-1, cell adhesion molecule 5.2 (CAM 5.2), a portion of CAM 5.2, a nucleic acid encoding a polypeptide comprising at least a portion of CAM 5.2, leptin, a portion of leptin, a nucleic acid encoding a polypeptide comprising at least a portion of leptin, Bcl-2 gene product, a portion of Bcl-2 gene product, a nucleic acid encoding a polypeptide comprising at least a portion of Bcl-2 gene product, nuclear matrix 23 (nm23), a portion of nm23, a nucleic acid encoding a polypeptide comprising at least a portion of nm23, an apoptosis-related protein, a portion of said protein, a nucleic acid encoding a polypeptide comprising at least a portion of the apoptosis-related protein, lipocalin NGAL, a portion of lipocalin NGAL, a nucleic acid encoding a polypeptide comprising at least a portion of lipocalin NGAL, complement regulatory protein CD 46, a portion of CD 46, a nucleic acid encoding a polypeptide comprising at least a portion of CD 46, complement regulatory protein CD 59, a portion of CD 59, a nucleic acid encoding a polypeptide comprising at least a portion of CD 59, a nucleic acid encoding a portion of an FHIT gene, loss of heterozygosity at an FRA3B site, MRP-1/CD9, a portion of MRP-1/CD9, a nucleic acid encoding a polypeptide comprising at least a portion of MRP-1/CD9, KA11/CD82, a portion of KA11/CD82, a nucleic acid encoding a polypeptide comprising at least a portion of KA11/CD82, a Fibroblast Growth Factor (FGF), a portion of FGF, a nucleic acid encoding a polypeptide comprising at least a portion of an FGF, Vascular Epithelial Growth Factor (VEGF), at least a portion of VEGF, a nucleic acid encoding a polypeptide comprising at least a portion of VEGF, Insulin-like Growth Factor-1 (IGF-1), at least a portion of IGF-1, a nucleic acid encoding a polypeptide comprising at least a portion of IGF-1, tumor amplified kinase STK15 (also BTAK and aurora2), a portion of STK15, a nucleic acid encoding a polypeptide comprising at least a portion of STK15, TMS-1, a portion of TMS-1, a nucleic acid encoding a polypeptide comprising at least a portion of TMS-1, maspin, at least a portion of maspin, a nucleic acid encoding a polypeptide comprising at least a portion of maspin, at least a portion of breast cancer associated (BRCA) gene, at least a portion of a BRCA gene product; CDw60protein, a portion of CDw60 protein or polypeptide, a nucleic acid encoding a polypeptide comprising at least a portion of CDw60protein or polypeptide, mammary expressed enzymes including cytochrome P450s, catechol-O-methyltransferase, epoxide hydrolase, peroxidases, glutathione S-transferases, N-acetyltransferases, or sulfotransferases, a nucleic acid encoding at least a portion of a mammary expressed enzyme, Kallikrein 6 (zyme/protease M/neurosin) protein or polypeptide (hK6), a nucleic acid encoding at least a portion of an hK6 protein or polypeptide; and mammastatin protein or polypeptide, and a nucleic acid encoding at least a portion of a mammastatin protein or polypeptide.

5. A method to aid in diagnosing breast cancer or pre-cancer comprising:
placing a ductal access tool comprising a single lumen in a breast duct of a patient, wherein the single lumen has an inner diameter large enough to retrieve clusters of greater than 10 cells:
infusing a fluid into the duct through the single lumen; and
retrieving a ductal fluid sample from the accessed duct through the single lumen, wherein the ductal fluid sample comprises ductal epithelial cells and is free of ductal fluid from any other duct of the breast; and:
examining the ductal fluid sample to determine absorption of a molecule by abnormal cells in the fluid.

6. A method as in claim 5, wherein the molecule comprises iodide.

7. A method as in claim 1, further comprising:
examining the ductal fluid sample for a loss of heterozygosity.

8. A method as in claim 1, further comprising examining the ductal fluid sample for the presence of two or more markers.

9. A method as in claim 1, further comprising examining the ductal fluid sample for the absence or two or mere markers.

10. A method as in claim 1, further comprising examining the ductal fluid sample for the presence of at least one marker and the absence of at least one marker.

11. A method as in claim 1, further comprising analyzing collected ductal epithelial cells by cytology.

12. A method as in claim 9, wherein the markers are selected from the group consisting of: DNA content, p53 gene or gene product, and G-actin or a nucleic acid encoding a polypeptide comprising at least a portion of G-actin.

13. A method for analyzing breast markers or epithelial cells, comprising:
placing a ductal access tool comprising a single lumen in a breast duct of a patient, wherein the single lumen has an inner diameter large enough to retrieve clusters of greater than 10 cells;
infusing a fluid into the duct through the single lumen;
retrieving a ductal fluid sample from the accessed duct through the single lumen, wherein the ductal fluid sample comprises ductal epithelial cells and is free of ductal fluid from any other duct of the breast; and
determining the presence or absence of a marker in the ductal fluid sample.

14. A method as in claim 13, wherein the duct from which the ductal fluid sample is retrieved is not spontaneously discharging ductal fluid.

15. A method as in claim 13, wherein the marker is selected from the group consisting of: lysophosphatidic acid, a lysophospholipid, palladin, a portion of palladin, a nucleic acid encoding a polypeptide comprising at least a portion of palladin Lg, a portion of Lg, a nucleic acid encoding a polypeptide comprising at least a portion of Lg, E2F1, a portion of E2F1, a nucleic acid encoding a polypeptide comprising at least a portion of E2F1, T1A12/mac 25, a portion of T1A12/mac 25, a nucleic acid encoding a polypeptide comprising at least a portion of T1A12/mac 25, MAGUK/ZO-1, a portion of MAGUK/ZO-1, a nucleic acid encoding a polypeptide comprising at least a portion of MAGUK/ZO-1, repressor of estrogen receptor activity (REA), a portion of REA, a nucleic acid encoding a polypeptide comprising at least a portion of REA, prothymosin alpha (PTA), a portion of PTA, a nucleic acid encoding a polypeptide comprising at least a portion of PTA, c-raf kinase, a portion of c-raf kinase, a nucleic acid encoding a polypeptide comprising at least a portion of c-raf kinase, CD66a, a portion of CD66a, a nucleic acid encoding a polypeptide comprising at least a portion of CD66a, KL-1, a portion of KL-1, a nucleic acid encoding a polypeptide comprising at least a portion of KL-1, cell adhesion molecule 5.2 (CAM 5.2), a portion of CAM 5.2, a nucleic acid encoding a polypeptide comprising at least a portion of CAM 5.2, leptin, a portion of leptin, a nucleic acid encoding a polypeptide comprising at least a portion of leptin, Bcl-2 gene product, a portion of Bcl-2 gene product, a nucleic acid encoding a polypeptide comprising at least a portion of Bcl-2 gene product, nuclear matrix 23 (nm23), a portion of nm23, a nucleic acid encoding a polypeptide comprising at least a portion of nm23, an apoptosis-related protein, a portion of said protein, a nucleic acid encoding a polypeptide comprising at least a portion of the apoptosis-related protein, lipocalin NGAL, a portion of lipocalin NGAL, a nucleic acid encoding a polypeptide comprising at least a portion of lipocalin NGAL, complement regulatory protein CD 46, a portion of CD 46, a nucleic acid encoding a polypeptide comprising at least a portion of CD 46, complement regulatory protein CD 59, a portion of CD 59, a nucleic acid encoding a polypeptide comprising at least a portion of CD 59, a nucleic acid encoding a portion of an FHIT gene, loss of heterozygosity at an FRA3B site, MRP-1/CD9, a portion of MRP-1/CD9, a nucleic acid encoding a polypeptide comprising at least a portion of MRP-1/CD9, KA11/CD82, a portion of KA11/CD82, a nucleic acid encoding a polypeptide comprising at least a portion of KA11/CD82, a Fibroblast Growth Factor (FGF), a portion of FGF, a nucleic acid encoding a polypeptide comprising at least a portion of an FGF, Vascular Epithelial Growth Factor (VEGF), at least a portion of VEGF, a nucleic acid encoding a polypeptide comprising at least a portion of VEGF, Insulin-like Growth Factor-1 (IGF-1), at least a portion of IGF-1, a nucleic acid encoding a polypeptide comprising at least portion of IGF-1, tumor amplified kinase STK15 (also BTAK and aurora2), a portion of STK15, a nucleic acid encoding a polypeptide comprising at least a portion of STK15, TMS-1, a portion of TMS-1, a nucleic acid encoding a polypeptide comprising at least a portion of TMS-1, maspin, at least a portion of maspin, a nucleic acid encoding a polypeptide comprising at least a portion of maspin, at least a portion of breast cancer associated (BRCA) gene, and at least a portion of a BRCA gene product; CDw60 protein, a portion of CDw60protein or polypeptide, a nucleic acid encoding a polypeptide comprising at least a portion of CDw60protein or polypeptide, mammary expressed enzymes including cytochrome P450s, catechol-O-methyltransferase, epoxide hydrolase, peroxidases, glutathione S transferases, N-acetyltransferases, or sulfotransferases, a nucleic acid encoding at least a portion of a mammary expressed enzyme, Kallikrein 6 (zyme/protease M/neurosin) protein or polypeptide (hK6), a nucleic acid encoding at least a portion of an hK6 protein or polypeptide; and mammastatin protein or polypeptide, and a nucleic acid encoding at least a portion of a mammastatin protein or polypeptide.

16. A method as in claim 13, wherein the marker is absorption of a molecule by abnormal cells in the fluid.

17. A method as in claim 16, wherein the molecule comprises iodide.

18. A method as in claim 13, wherein the marker is a loss of heterozygosity.

19. A method as in claim 13, wherein the presence of two or more markers is determined.

20. A method as in claim 13, wherein the absence of two or more markers is determined.

21. A method as in claim 13 wherein the presence of at least one marker and the absence of at least one marker is determined.

22. A method as in claim 13 wherein the marker determined is cytology of ductal epithelial cells.

23. A method as in claim 13, wherein the marker is selected from the group consisting of DNA content, p53 gene or gene product, and G-actin or a nucleic acid encoding a polypeptide comprising at least a portion of G-actin.

* * * * *